(12) United States Patent
Bryant (10) Patent No.: US 9,387,112 B2
(45) Date of Patent: Jul. 12, 2016

(54) MYOELECTRIC HAND ORTHOSIS

(71) Applicant: Marvin Frank Bryant, Smryna, GA (US)

(72) Inventor: Marvin Frank Bryant, Smryna, GA (US)

( * ) Notice: Subject to any disclaimer, the term of this patent is extended or adjusted under 35 U.S.C. 154(b) by 206 days.

(21) Appl. No.: 14/192,364

(22) Filed: Feb. 27, 2014

(65) Prior Publication Data

US 2014/0243721 A1  Aug. 28, 2014

Related U.S. Application Data

(60) Provisional application No. 61/770,319, filed on Feb. 28, 2013.

(51) Int. Cl.
*A61F 5/00* (2006.01)
*A61F 5/01* (2006.01)

(52) U.S. Cl.
CPC ..................... *A61F 5/013* (2013.01)

(58) Field of Classification Search
CPC ........... A63B 2102/18; A63B 2209/00; A63B 2210/50; A63B 2225/09; A63B 59/50; A63B 60/04; A63B 60/16; A63B 60/42; A63B 71/0045; A63B 2209/10; A63B 59/0074; A63B 59/06; A63B 60/52; A63B 60/54; A63B 69/3635; A63B 21/4025; A63B 23/16; A63B 21/4017; A63B 21/4019; A63B 21/4021; A63B 21/00069; A63B 21/055; G06T 19/20; G06T 2219/2016; G06T 2219/2021; A61B 5/1411; A61B 5/151; A61B 6/4258; A63H 23/10; B63B 35/7993; E05G 1/005; E05G 1/12; E05G 2700/04; F41A 19/39; F41A 3/26; A61F 5/0118; A61F 5/05866; A61F 5/013; A61F 2005/0179; A61F 5/10; A61F 5/3761; A61F 2002/704; A61F 2/68; A61F 2/72; A61F 2002/701; A61F 2002/7635; A61F 2002/7625; A61F 2/583; A61F 2002/7645; A61F 2002/764; A61F 2/586; A61F 2/6607; A61F 2002/6827; A61F 2/64
USPC ............................... 602/20–22; 128/778–779
See application file for complete search history.

(56) References Cited

U.S. PATENT DOCUMENTS

| | | | | |
|---|---|---|---|---|
| 867,981 | A * | 10/1907 | Krizek | A63B 23/16 482/48 |
| 3,631,542 | A * | 1/1972 | Potter | A61F 2/72 601/40 |
| 4,167,044 | A | 9/1979 | Girard | |
| 4,602,620 | A * | 7/1986 | Marx | A61F 5/10 602/21 |
| 4,765,320 | A * | 8/1988 | Lindemann | A61F 5/0118 602/22 |
| 6,312,398 | B1 | 11/2001 | Cencer | |
| 6,379,393 | B1 | 4/2002 | Mavroidis et al. | |

(Continued)

FOREIGN PATENT DOCUMENTS

| | | |
|---|---|---|
| JP | 2001046450 | 2/2001 |
| JP | 2002345861 | 12/2002 |

(Continued)

*Primary Examiner* — Michael Brown
(74) *Attorney, Agent, or Firm* — David L. King (57) ABSTRACT

The present invention relates to an orthotic glove intended to be worn by a human hand and be used for assisting or controlling movement of one or more fingers of the hand, the thumb, and/or the wrist in response to an input signal and methods related thereto. The finger is animated by the shape recovery of a shape memory alloy wire. The invention further relates to a microprocessor-controlled, electromechanical hand orthosis to provide functional use of a hand.

2 Claims, 9 Drawing Sheets

(56) References Cited

U.S. PATENT DOCUMENTS

| | | |
|---|---|---|
| 7,481,782 B2 | 1/2009 | Scott et al. |
| 8,328,743 B2 * | 12/2012 | Farrell ................ A63B 23/16 602/20 |
| 2006/0094989 A1 | 5/2006 | Scott et al. |
| 2009/0326428 A1 | 12/2009 | Farrell et al. |
| 2010/0041521 A1 | 2/2010 | Ingvast et al. |
| 2010/0198115 A1 | 8/2010 | Koeneman et al. |
| 2010/0249675 A1 | 9/2010 | Fujimoto et al. |
| 2010/0249676 A1 | 9/2010 | Kawakami |
| 2012/0022666 A1 | 1/2012 | Brooks et al. |
| 2012/0029399 A1 | 2/2012 | Sankai |

FOREIGN PATENT DOCUMENTS

| | | |
|---|---|---|
| JP | 2004267254 | 9/2004 |
| JP | 2004298573 | 10/2004 |
| JP | 2004329490 | 11/2004 |
| JP | 2005073714 | 3/2005 |
| JP | 2007275486 | 10/2007 |
| JP | 2008067852 | 3/2008 |

* cited by examiner

MYOELECTRIC HAND ORTHOSIS

FIELD OF USE

The present invention relates to an orthotic glove intended to be worn by a human hand and be used for assisting or controlling movement of one or more fingers of the hand, the thumb, and/or the wrist in response to an input signal and methods related thereto. The finger is animated by the shape recovery of a shape memory alloy wire. The invention further relates to a microprocessor-controlled, electromechanical hand orthosis to provide functional use of a hand.

BACKGROUND

Loss of finger or hand function severely affects an individual's ability to perform manual tasks. Prior orthotic devices have restored limited hand function to individuals unable to control finger movement. These devices use robotic technologies and actuate fingers through use of motors or other mechanisms.

There are myoelectric devices for the purpose of enhancing or restoring functional use of the hands of those who have a disability of the upper extremity distal to the elbow. Prior art myoelectric devices are large, bulky devices. They also often require large and heavy batteries due to the amounts of electrical current and/or voltage needed to power them.

Other orthotic devices have used shape memory alloy wires made of Nitinol or like materials as actuating members. The Nitinol wire forms part of an electrical circuit that selectively flows current through the Nitinol wire to heat the wire to a transition temperature that contracts the wire. The wire contraction actuates a member joined to an orthotic to move an otherwise uncontrollable finger.

US 2006/094989 discloses a movement facilitation device for the movement of a joint or limb. It uses shape memory alloy wires in one embodiment that contract to provide movement to a joint. This device is for therapeutic rehabilitation and does not offer active control over strength or range of motion.

The use of shape memory alloy wire's contraction to actuate orthotic devices is problematic. A long Nitinol wire is usually required to generate a sufficient contraction stroke for finger actuation. Heated Nitinol wire only shrinks about 3% of its unheated length. The long wire length necessitates prior orthotic devices to include large support portions to accommodate the coils of long shape memory alloy wires.

Another problem with prior orthotic devices that use SMA is with heat. Some rely on radiation to cool the coils of long, hot, contracted wire below the transition temperature and return the wire to its original length prior to another contraction. Radiation cooling slows wire relaxation/lengthening and causes a time delay before the joint can be moved again.

US Patent Application 2012/0022666 discloses a system for moving a prosthetic finger. The device could be a glove worn over a damaged finger. It uses shape memory alloy wire to articulate the finger. The device includes a cooling system for each wire. It uses the contraction of the length of wire when heated above transition temperature to create tension on another wire running along the top of the finger. This then pulls more wires to create movement of the finger at each joint. This is a bulky and complex system of heating and cooling shape memory alloy wires.

Accordingly, there is a need for an orthotic device that is portable and that will comfortably, safely, and intuitively restore the functional use of the hand or hands of those who are disabled. The preferred device would be myoelectric, lightweight, slim, and energy efficient—requiring relatively few small batteries and making it safe and comfortable to wear all day. There is a further need for an orthotic device that provides individual, articulate control over each joint of each finger, which allows for control over the range of motion and force by which each joint is moved.

SUMMARY OF THE INVENTION

The method and the system of the present invention centers around the concept of providing a portable device that will enhance or restore functional use of the hand. The present invention is cosmetically attractive, uses few, small, light batteries, is safe for the user to wear and operate, easy to don and doff, able to perform for long periods of time between recharging cycles, and comfortable enough to be worn all day and on a daily basis. The present invention is slim, lightweight, easy to use, and energy efficient, using multiple short sections of relatively thin Nitinol wires or sheets to provide the necessary movements.

The device is predominantly for use by the handicapped but is not limited to this user group. Typical pathologies include C-4, C-5, and some C-6 level Quadriplegia or tetraplegia (spinal cord injury), TBI, Polio, stroke, Lou Gehrig's disease, brachial plexus or other peripheral nerve injuries, muscular dystrophy, atrophy, cerebral palsy, and multiple sclerosis. One embodiment will also operate as a myoelectric prosthetic for those with an amputation of the finger(s), hand or forearm distal to the elbow.

The device, in one embodiment, includes a support member worn around the forearm that may contain one or more of the following: the power supply, bioelectric sensors, microprocessor, and appropriate circuitry. Another support member is worn around the hand and attaches to the forearm support member by a flexible material. Shape memory alloy, SMA, actuators attach to the hand support on one end and to rings encircling the finger of the hand on the other end. The forearm and hand supports may comprise of any material that is thin, lightweight, and rigid e.g. ABS, nylon, aluminum, carbon fiber, thermoplastic, PVC, etc. If not sewn into the liner of a glove, they should be sufficiently padded to protect the wearer from chafing and have straps or an elastic membrane to secure them to the body. The actuators to which the SMA wires attach are comprised of two materials: an elastic or flexible component such as rubber or nylon and a light, rigid component like the support members. The rings can be of the same or different light rigid material. The actuators and rings may be printed on a 3D printer and be comprised of the plastic and elastic component therein.

In one embodiment, there is an additional support structure over the thumb attached to the hand support by a flexible membrane and an actuator. There may also be an actuator connecting the hand support to the forearm to assist in flexion of the wrist or radiocarpal joint.

In a preferred embodiment, bioelectric, temperature, and thin pressure sensors will provide the inputs to the electrical system and batteries provide the electrical power. Triggering the device to activate can be achieved through the use of myoelectric switching by means of electrical impulses in operative muscles picked up by bioelectric sensors attached to the wearer's skin. The signal is filtered and amplified to produce a voltage that is read by a microprocessor. The microprocessor determines which actuators to activate or deactivate and in what sequence to do so to animate the appropriate joint proportionately to the users wishes. The actuator or attached ring will contain a thin pressure sensor, such as a thin-film transducer, to monitor the applied force. This input signal will also be processed and then read by the microprocessor to determine which actuator to deactivate when a predetermined maximum amount of force has been applied.

While most prior art using SMA use coils of long lengths Nitinol wires for their contraction when heated above their transition temperature, the present invention uses relatively short lengths of wire or small sheets, strips, screens and takes advantage of the shape memory effect of Nitinol. In the present application, the term "wires" will be defined as the Nitinol material spanning the supports which could be a wire, a cord, a flat rectangular strip, a sheet or screen of Nitinol material. The shape or configuration can be any of these shapes, but for convenience these are collectively called a "wire". The short sections of wire bridge across the blocks that are the sections of the actuator. These wires are bent between gaps in the actuator and when activated by electrical current straighten, pushing the sections apart. When activated, the actuators move in an arc because of the way the blocks are designed and attached within the actuator. By controlling the number of actuator blocks, the geometry of the actuator and actuator blocks, and the size and length of wire allows for a choice in designing for the strength, range of motion, and the precision of movement for a device.

The SMA actuators align along the outside top of the joint. When activated, the actuator moves in an arc over or around the joint providing the desired movement of the joint over which it is attached. In one embodiment, the elastic component of the actuator is use to return the joint to its passive, pre-flexed position. In another embodiment, additional SMA that have been annealed in a bent configuration are used to contract the actuator and appropriate joint.

In one embodiment, the SMA actuators are mounted at each joint of the finger, thumb, and wrist. In further embodiments, the SMA actuators are provided at only certain joints. In still further embodiments, there are caps at the fingers' tips and may contain additional thin pressure or temperature sensors.

In a preferred embodiment, the software is modular and able to be adapted to each user's individual needs or desires for which joints can move and with what strength and range of motion the joint can be moved through.

It is to be understood that both the foregoing general description and the following detailed description are exemplary and explanatory only and are not restrictive of the invention, as claimed.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DESCRIPTION OF THE EMBODIMENTS

Researchers in rehabilitation engineering design orthoses to compensate or substitute for an impaired organism by offering either a more normal function or an alternate mode of function. A major function of the hand orthosis is to provide the ability to pinch, grip, and release objects during daily living activities. The ideal hand orthosis uses the skeletal structure and the biomechanical properties of the user's limb as an integral part of its powered mechanical system.

The present disclosure relates to the area of myoelectric orthotic systems and methods of making and using the systems. The description that follows relates to a myoelectric hand orthosis. However, it is to be understood that the while the present disclosure lends itself well to applications in assistive device technology, the disclosure, in its broadest aspects, may not be so limited. Rather, the present disclosure may be used with any type of orthotic system.

The device of the invention is generally a microprocessor-controlled, electromechanical hand orthosis. It is useful for those who wish to enhance or restore functional use of one or more joints of the fingers of the hand and/or the wrist. It accomplishes this by combining various technologies into one device, which will read the nerve impulses through the skin of the wearer's forearm, draw the necessary electricity from batteries, and activate actuators forcing the finger(s) to move. The device operates in accordance with and proportionally to the bioelectric potentials picked-up by surface electrodes placed on the surface of the forearm.

The actuator is preferably a multi-staged block system of rigid sections connected by short lengths shape memory alloy wire/ribbon/sheet/screen/foil that cause the sections of the block to move. The device can be customized for each individual user's specific needs. The description that follows relates to a myoelectric hand orthotic system. However, it is to be understood that while the present disclosure lends itself well to applications in hand orthotics, the disclosure, in its broadest aspects, may not be so limited. The device is compatible with the daily activities of the user without bulky or cumbersome interference.

The invention comprises one or more of the following functional components: structural frame, bioelectric sensors, circuit board, a band-pass filter, a half-wave rectifier, a micro-controller, a pulse width modulation circuit, batteries, actuators, shape memory alloy (SMA), thin pressure sensors, temperature sensors, thermoelectric coolers and software. The circuit board may consist of an instrumentation amplifier. The band-pass filter may be high-pass and low-pass filters in series.

Figure 1A:
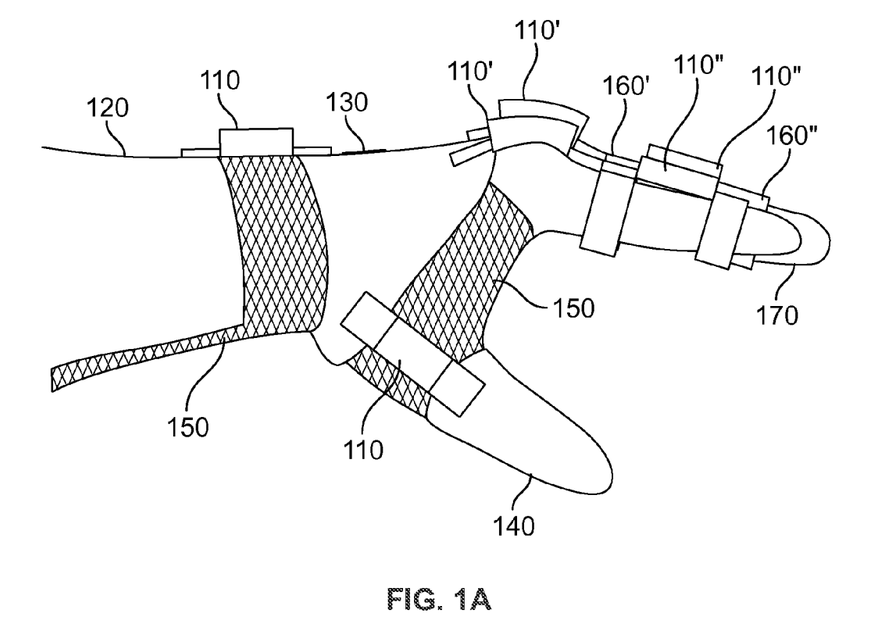
FIG. 1A is a side view of one embodiment of the present invention illustrating the device in a non-activated position.
Figure 1B:
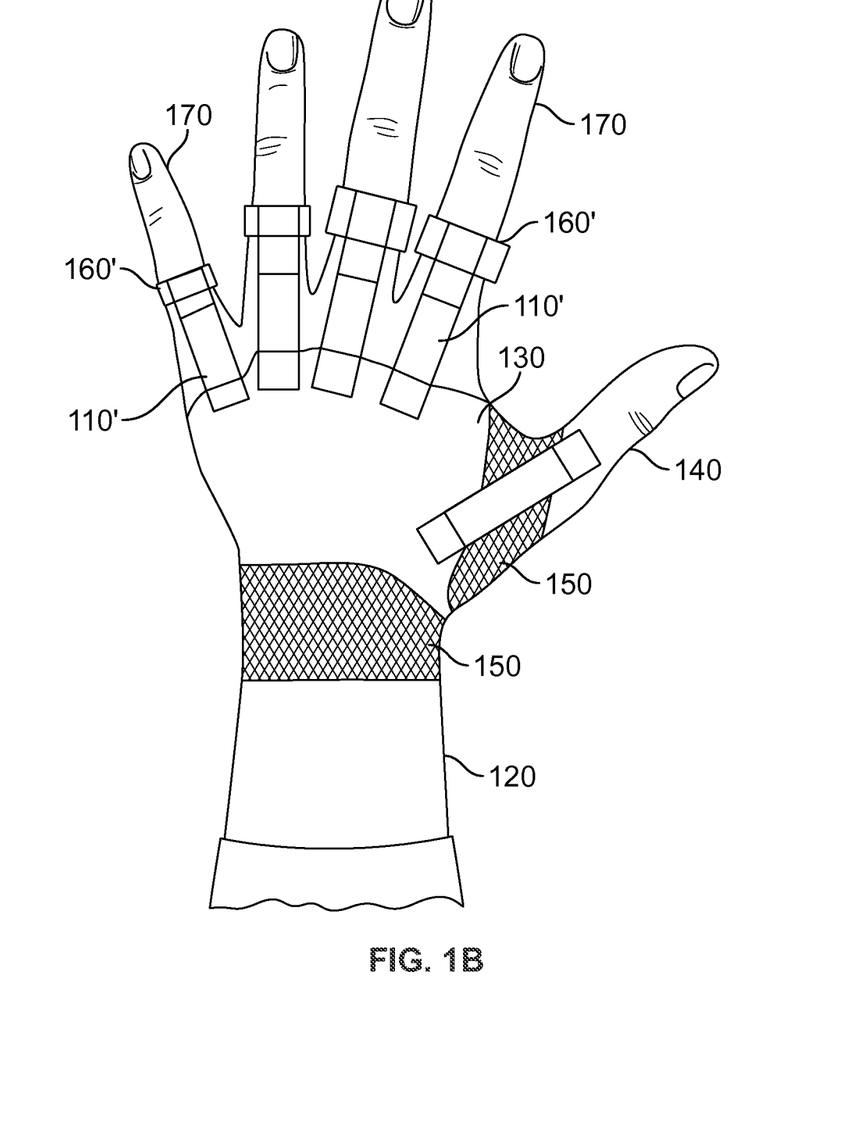
FIG. 1B is a top view of another embodiment.

FIG. 1A, illustrates one embodiment of a myoelectric hand orthosis device 100. The device comprises two parts: a hand piece 130 and a forearm piece 120 that are spanned by a flexible membrane 150. The hand piece may be adapted to fit any hand size. The hand piece 130 is designed to fit between the wrist and the metacarpal joints and to support one end of the actuators 110 for the wrist and each of the 5 metacarpal joints. In an embodiment of the invention a pair of actuators 110', 110" are provided. The second set of actuators 110" are preferably connected to one end to a first set of rings 160' and at the other end to a second set of rings 160". In another embodiment of the invention shown in FIG. 1B actuators are provided for only the metacarpophalangeal joints. Each actuator 110 and a first set of actuators 110' are connected at one end to the hand piece 130 and at the other end to a finger by way of a ring 160 in a first set of rings 160'. At least one ring 160 preferably encircles each finger 170 and preferably, at least a first set of rings 160', 160" comprising two or more rings is provided per hand. In one embodiment, the device terminates with caps enclosing the fingers' tips.

The hand piece 130 may also comprise of a support member for the thumb 140 that is connected to the hand piece 130 by an actuator 110. The hand piece 130 is preferably designed to fit over and around the hand by way of an elastic membrane 150 but may also be secured using straps such as Velcro. In an embodiment of the invention, the actuators 110 are preferably attached to each finger, the thumb, and the forearm.

Figure 2A:
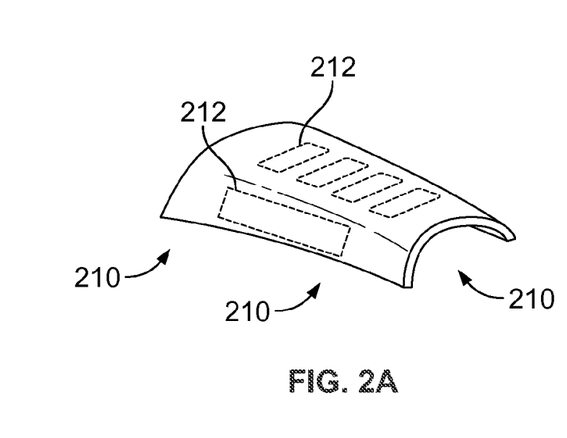
FIG. 2A is a perspective top view of the forearm portion of the device with a circuit and batteries shown in dashed lines.
Figure 2B:
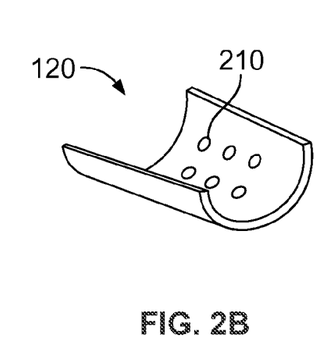
FIG. 2B is a perspective underside view of the forearm portion of the device.

As shown in FIGS. 2A and 2B, the forearm piece 120 houses the device's hardware, including the surface electrodes sensors 210, a battery 212 and a control circuit 214 comprising a microprocessor. Any suitable bioelectric sensor may be used. A preferable surface electrode is an EMG sensor 210. The battery(s) is preferably rechargeable. In an embodiment of the invention, bioelectric sensors 210 are attached to the control circuit's inputs at one end and attached to the skin at the other end (not shown). In an embodiment of the invention, the bioelectric sensors 210 align with the target muscle(s), that is, with the wrist extensors and the wrist flexors (target muscles vary with the patient).

The bioelectric sensors and thin force sensors (not shown) provide input. The batteries provide electrical energy to the device. The circuit board comprises of suitable electronics to process the input signals from the bioelectric sensors, as well as to provide the desired output to the actuators. TEC and pressure sensors may be located at each actuator. The TEC are for thermal sensing and protection, and the pressure sensors detect the amount of force applied by the device. All components are essential for function except for the TEC and pressure sensors. One reason that they are included is for the protection of the device, the user, and others. Monitoring of the pressure sensors also allows for precise control of the power and range of motion of the device.

Figure 3:
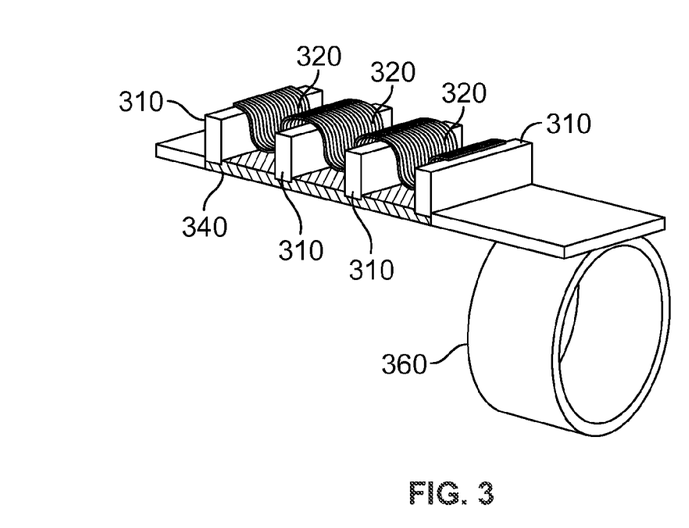
FIG. 3 is a view of one of the actuators illustrated in FIG. 1.

Actuators 110, as shown in detail in FIG. 3, receive output from a microprocessor and provide the mechanical work to move the appropriate joints. In one embodiment, the actuator 110 is connected to a finger by a ring member 360, which attaches to the actuator and encircles the finger.

Referring to FIG. 3, multiple actuator blocks 310 flexibly connect to each other via base elastic connector 340 and flexible wire 320. The base connector 340 is preferably formed from a flexible, yet elastic, material. The flexible wires 320 act as the "motors" that drive the device. The flexible wires 320 are preferably shaped memory alloy (SMA) wires/sheet.

Figure 4:
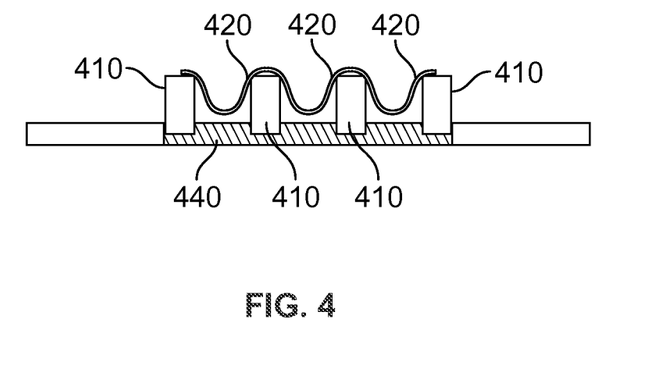
FIG. 4 is a side view of one actuator not activated.
Figure 5:
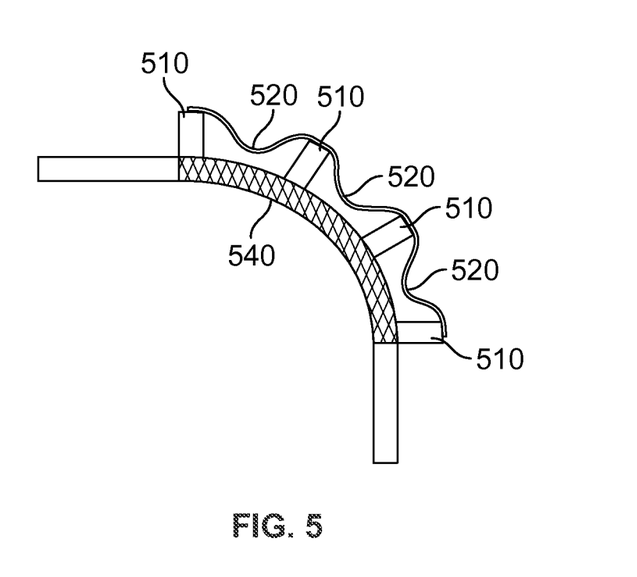
FIG. 5 is a side view of one actuator activated.

Referring now to FIGS. 4 and 5, prior to activation, the actuator blocks 410 are in a parallel position to one another and perpendicular to the connector material 440, which is an un-stretched state. The SMA wires 420 are in a curved or bent state. When the device is activated, an electrical current heat the SMA wires 520 and causes them to straighten. Because of the way in which the blocks are mounted, this straightening causes the actuator to move in an arc, curving around and bending the appropriate joints. When the SMA wires 520 straighten, they push apart the actuator blocks 510, which move in an angle as shown. The base connector 540 bends or forms into a stretched state.

SMA is preferred for its ability to return to a programmed position when heated above its transition temperature. Preferably, short lengths (less than 10 mm) of small wire (less than 0.15 mm in diameter) are used.

The geometry between the height of the actuator blocks and the distance the tops of them move (how much the SMA is bent) and the number of sections determine the angle through which the device moves. The material can only be strained 3% or 4% and still ensure long-term repeatability. These drawings allow for three sections to move 30 degrees each for a total of 90 degrees. Adding sections, changing their geometry, and changing the wire size/bend can allow for more precision of movement (smaller angles of movement for each section).

One preferred configuration uses (19×3=57) 0.004" wires for each actuator to achieve a preferred size, strength and range of motion. Other configurations use more or less and/or wires of smaller and larger diameters and lengths. The advantage of using wire is that one can connect a circuit to them in such a way as to control how many and which ones are to be activated at any one time. This is useful in controlling the strength and range of motion by which the actuators move to close the fingers. Because the wires are thin and spaced apart, they also allow for rapid heating and cooling and eliminate the need for any active cooling.

There may also be thin pressure sensors to measure the force exerted by each actuator. This will allow the microprocessor to disengage electric current to the actuator before it is overstrained and/or the wearer is injured. This also allows for near analog control over the range of motion and strength of grip as the current heating the SMA may be turned off before it finishes reaching the austenite phase.

Figure 6:
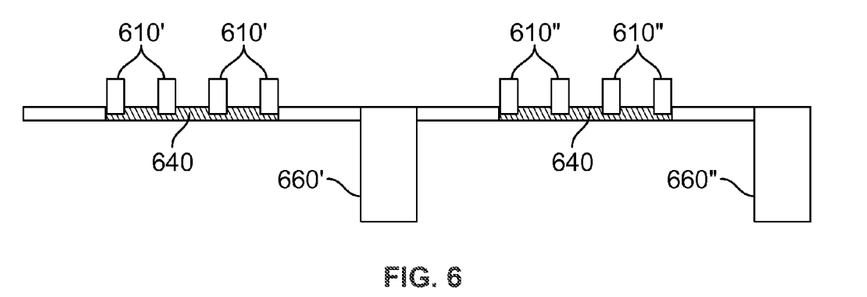
FIG. 6 is a side view of two attached actuators and their attached rings.
Figure 7:
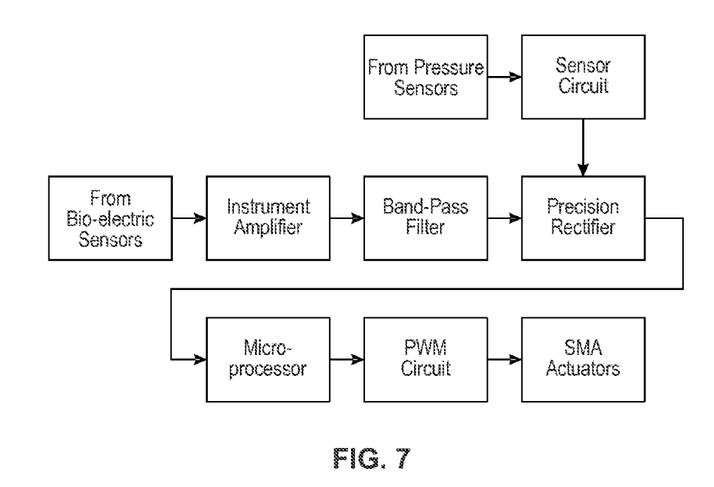
FIG. 7 is a diagrammatic representation of the electrical system according to one embodiment.

Referring to FIG. 6, in a second embodiment, of the invention two sets of actuator blocks 610', 610" and two sets of rings 660', 660" are attached in sequence on base connector 640 to bend the metacarpophalangeal joint, MP, and proximal interphalangeal joint, PIP, respectively.

Figure 14:
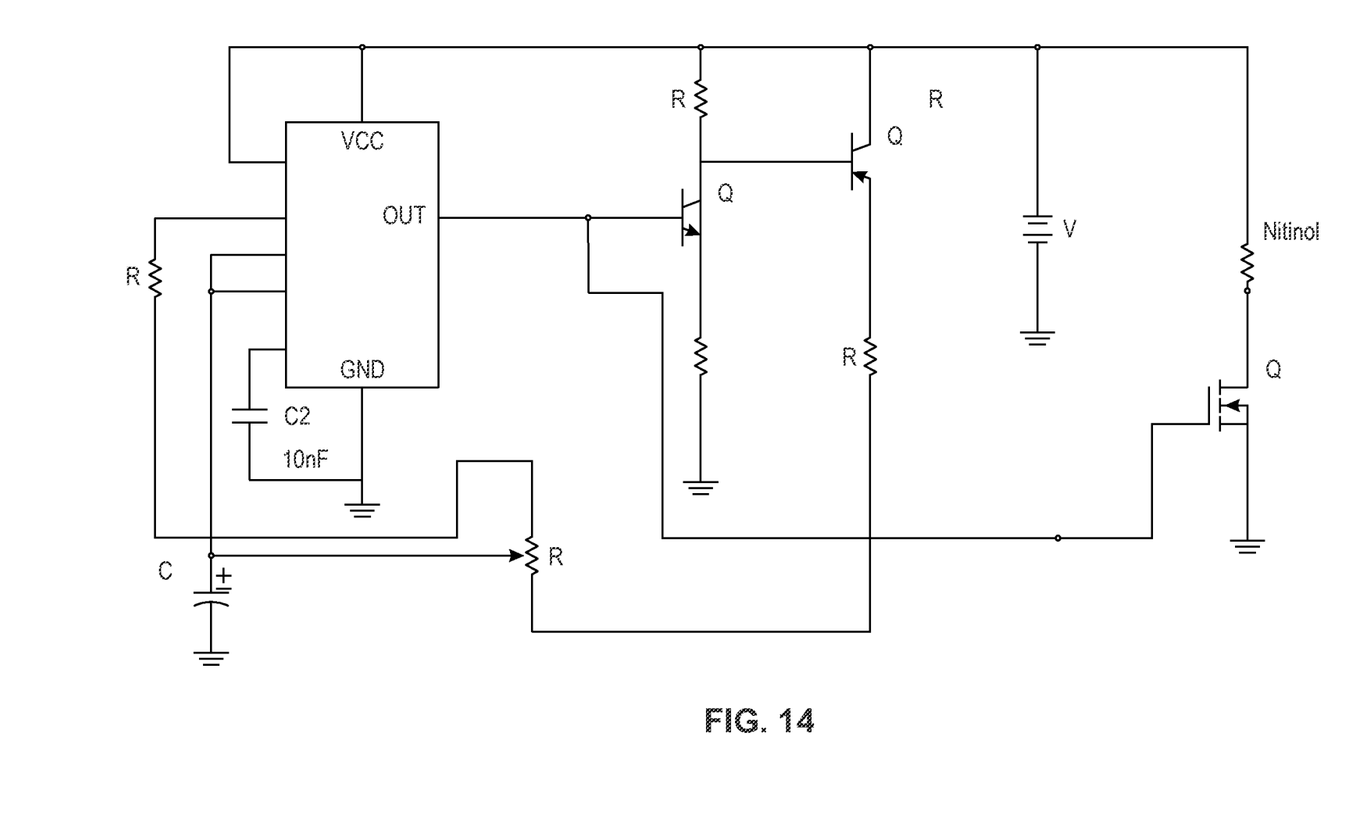
FIG. 14 is a circuit diagram of a pulse-width modulation circuit.

In a preferred embodiment, bioelectric sensors wired to the circuitry in the forearm will attach to the wearers skin. As shown in FIGS. 7 and 10-13, the signal from the bioelectric sensors will pass through an instrumentation amplifier, a band-pass filter (high-pass and low-pass filters in series), and a half-wave rectifier before entering the micro-controller. In an embodiment, the controller is programmed to take these outputs and pass the signal to a pulse width modulation circuit as shown in FIG. 14 to activate the appropriate actuator blocks. These actuators 110', 110" will bend over the finger joint pushing the finger down with them. They will contain thin force sensors for detecting the applied force and let the microprocessor know when to turn off current to the SMA actuators to protect the device and its wearer.

Figure 8:
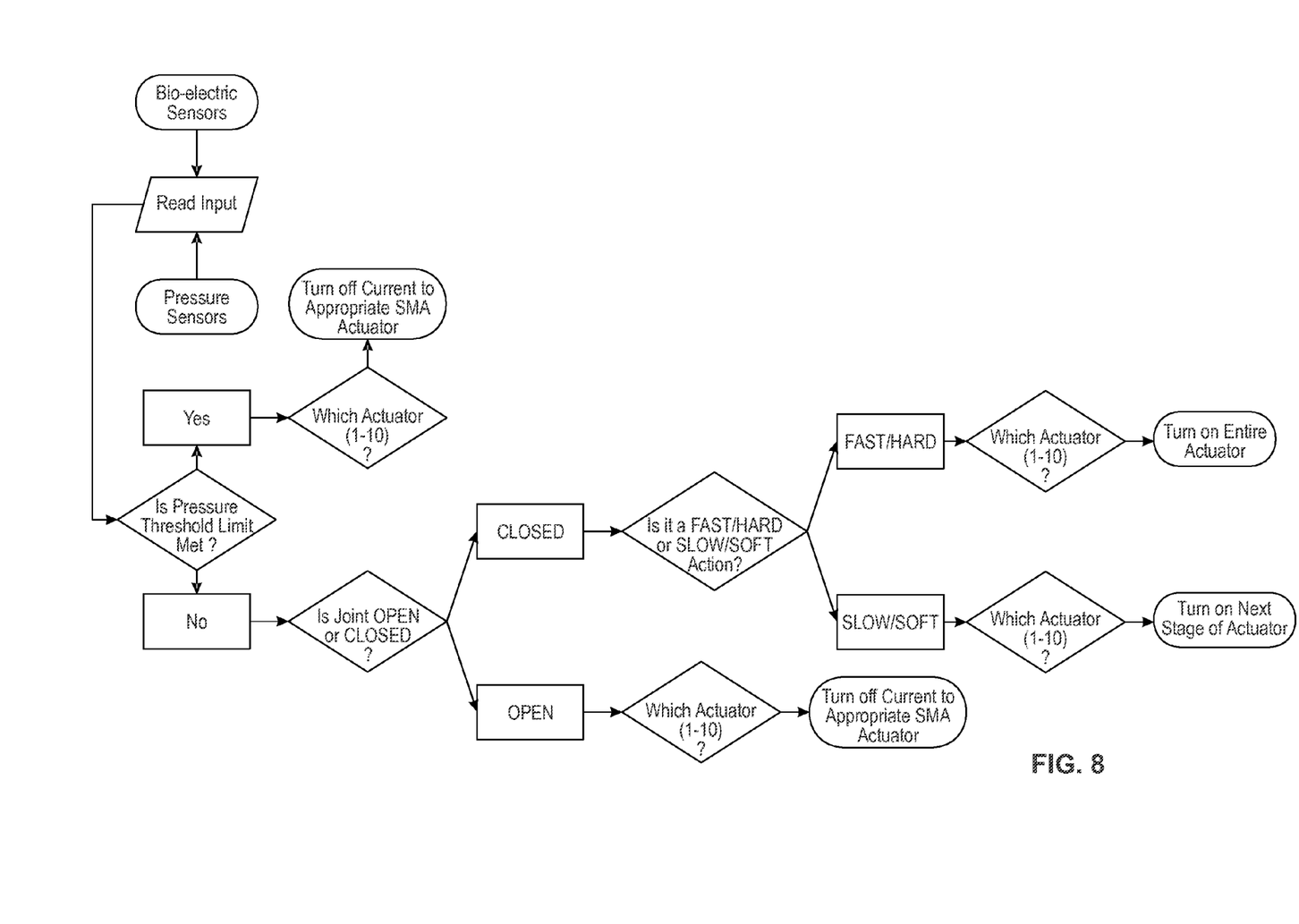
FIG. 8 is a diagrammatic representation of the operating software according to one embodiment.

Referring to FIG. 8, a micro-controller may be programmed to activate the SMA wires in accordance with the wearer's intentions. The device activates the appropriate actuator, does so in a sequence proportionate to changes in the input signal strength, and disengages the current when the bioelectric sensors or force sensors indicate. The skeletal frame, actuators, and electronics may be sewn into the liner of a glove or worn as an exoskeleton.

The components of the circuit board and other electronic components may be substituted with standalone devices and/or programming. The SMA wires may be replaced with other small linear actuators, for example, voice coils. The shape and size of the bend and mounting location of the SMA wire may be any suitable size, shape, or mounting location. The number and geometry of moving sections of the actuator block may be any suitable number or geometry.

In an embodiment of the invention, shaped memory alloy sheets/ribbons are used as a substitute for SMA wire. The number of ribbons, their mounting location, and size may also be varied. The elastic material can be replaced with more SMA wires or ribbons to return the joint to its passive or starting position. Any suitable power source may be used, for example solar cells or other electric sources.

In one embodiment, multiple bioelectric sensors are used along the top and bottom of the forearm to allow for differentiation between which muscles are being used and to therefore know which joint is being moved and how much. This will provide for a fully articulate control of all joints of the hand. In another embodiment, bioelectric sensors may be omitted or replaced with any other means to trigger activation of the device, including anything from an oral activator to buttons to an I-Pad. Components can be sewn into or attached to the outer surface of a glove. Device and components can be covered or made from any material. Device can be made to only assist the joint or joints in need. The glove can cover from all to none of the joints of the hand, including the finger thumb, or wrist.

An advantage of the present invention is that it does not use gears, cables, or pulleys. It also does not use conventional electric motors or linear actuators. The invention provides for a smooth, form-fitting, microprocessor-controlled glove that will read the wearers intentions and move accordingly with a hand inside of it. The device of the invention will fit under clothing and can be finished in any suitable covering. Moreover, the invention offers individual articulation of each joint of the finger and hand with control over the angle of degree and force each joint is moved. Additionally, using SMA wires in this way requires less electrical power than conventional myoelectric orthosis devices allowing for a much safer, lighter product and the use of comparatively fewer and smaller batteries.

Another benefit of the current inventions is that it is relatively low in cost compared to conventional prosthetic devices. Unlike the other alternatives, this device can be produced without the need to build a custom unit or for each person. A certain number of sizes can be made having adjustable software systems.

Shape memory alloy can be any number of alloys. The most common was also the first discovered, Nitinol—a Nickel-Titanium alloy that is at a ratio of roughly 55% Ni & 45% Ti. The wires can use other ratios of NiTi or other shape memory alloys as well as other linear actuators.

The maximum recoverable strain-limit for shape memory NiTi is about 6% to 8%. However, 3% to 4% is the recommended limit for product design. The ductility of NiTi wire that has been cold worked and heat-treated is typically 10% to 20% in tension. Fully annealed NiTi wire has a ductility limit of about 60% to 70%. Strain=radius of wire/(radius of curvature+radius of wire).

Figure 9:
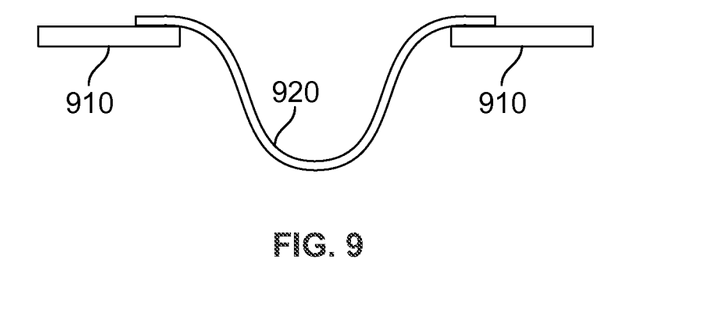
FIG. 9 is a side view of one SMA wire mounted.
Figure 10:
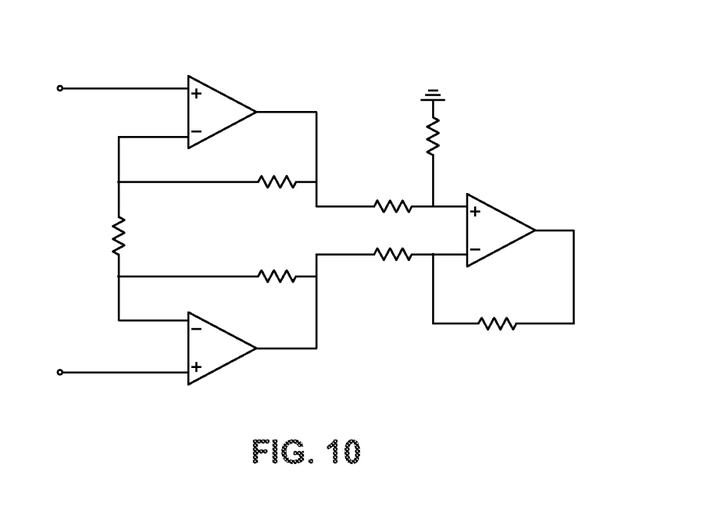
FIG. 10 is a circuit diagram of an instrument amplifier.
Figure 11:
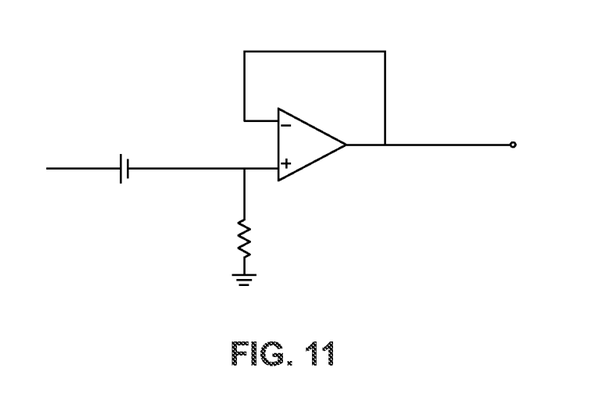
FIG. 11 is a circuit diagram of a high-pass filter.
Figure 12:
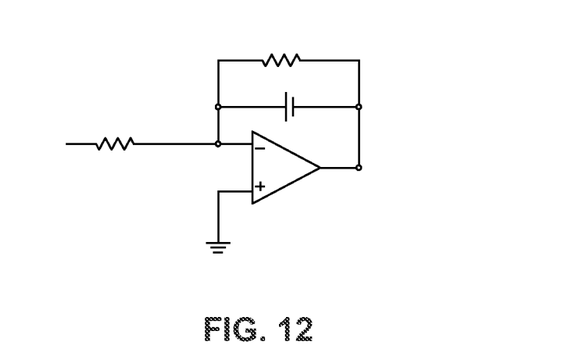
FIG. 12 is a circuit diagram of a low-pass filter.
Figure 13:
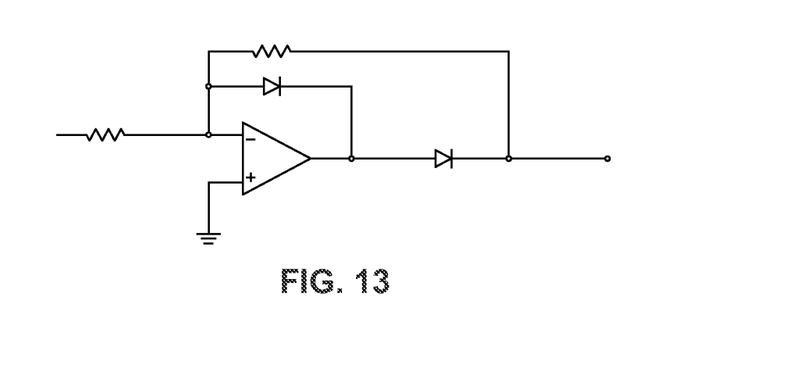
FIG. 13 is a circuit diagram of a half-wave rectifier.

In an embodiment, the SMA wire or sheet bends 3 times: once on each end where it mounts and in the middle FIG. 9. The radius of curvature is determined by the wires diameter and the amount of strain to be used.

This determines how close the moveable sections of the actuator blocks can be (Distance=4*r) and therefore how short the wire can be, Wire Length=Circumference (2*pi*r)+ some length for mounting to the blocks if mounting to their tops. This also determines how far the block will be pushed apart when the wire straightens, Circumference minus Distance or 2*pi*r−4*r=2.28*r. One can decide how many sections each actuator is to have and how many degrees those sections need to be moved. For example, if 90 degrees of movement for the actuator is desired, divide the number of sections into 90 to get determine how many degrees each section will need to move. Then use the Sine rule, Sine(theta)=opposite/hypotenuse, to determine the height each block needs to be to get the angle of motion desired. Height=2.28*r/Sine(theta). The height of the actuator blocks, thickness of the base connector (214) height of the protrusion of the SMA wire above the actuator blocks (2*r) are also determined. Preferably, one would include some cover high enough to protect the wires & allow them to cool.

Because of the Sine rule, the smaller the angle each section moves means it must get taller for a given section length, and the length is determined by the wire diameter or cross sectional area because of strain limits on bending it. A shorter section means smaller and less powerful wires and a less powerful device unless more wires are added or an increase in cross sectional area.

There is also the stress put on the wire when it straightens. If the wire tries to straighten and there is too much resistance, it will over stress the wire. This can be monitored by a pressure sensor at each of the actuators. Any suitable means for monitoring force may be used, but preferably, a thin-film transducer is used. Monitoring the forces being applied by the actuators with the microprocessor and turning off current when certain thresholds are met protects the device from over stress and the wearer from bodily injury. Any suitable amount of elasticity in the base connector may be used. Preferable there is enough elasticity to bend the wires back to their curved/bent position and straighten the actuator and finger when the current disengages and the wire cools. However, too much elasticity can create too much resistance, which can over stress the wire when it activates, and cause one to lose grasping force. Additional SMA wires may be included or substituted to provide this function.

A preferred SMA wire can exert from 20,000 psi up to 70,000 psi or more. A more preferred pressure is around 25,000 psi (172 MPa). When cool, the SMA wires can preferably be bent with between 10,000 psi and 20,000 psi of force. The elasticity of the base connector of the actuator block will depend on how many wires and what diameter is used. Otherwise, it may be preferable to use additional SMA material to pull the actuator and finger back up to a straight position.

Any suitable current and voltage may be used. For a given wire diameter there is a certain resistance per unit length (ohms/meter), resistance=resistivity/cross-sectional area where resistivity=rho*(1+temperature coefficient of resistivity*delta T). By adding up each section of wire length that is to be activated, one can calculate the total resistance. The amount of current needed to heat the wire in a reasonable amount of time is then calculated. Any suitable current may be used. Higher current will heat more quickly. Preferably, a suitable current would be below 300 mA DC with complete heating within 1 second. Current will be dependent on the diameter, length of wire sections, & the number of sections to be activated at a time. Once current and resistance are determined, voltage (V=IR) and power (W=V*I) requirements may be set. It should be understood that any changes to actuator size or geometry changes the wire size because of strain limits and therefore changes the electrical requirements.

The myoelectric orthotic device in addition to an assistive device for an impaired hand can work in rehabilitation. Therapists can use it as a therapeutic tool to reverse some disabilities. The device can be enhanced by adding both a neural interface for even lock-in patients to use their hands and some haptic technology to use on patients, especially comatose, soon after injury prevent disabilities from ever forming.

It is believed to be preferable to use sheets or strips of Nitinol rather than round wires. The device may be used with Myo Arm Bands instead of programming for the bioelectric sensors. One model just reads hand closure for patients with extensive nerve damage. It will still close articulately by reading force sensors to know when to stop closing each joint. There will likely be pressure sensors at each actuator for all renditions to protect the user from injury and control the movement of the device. Pressure and/or temperature sensors can be added to the finger tips to prevent wearers from injury as most have lost the sense of touch in the affected limb.

These and other variations are all considered in the scope of the present invention.

While the present disclosure has been described by means of specific embodiments and applications thereof, numerous modifications and variations could be made thereto by those skilled in the art without departing from the scope of the present disclosure.

I claim:

1. A myoelectric orthotic device comprising:
a hand piece;
a forearm piece, the forearm piece includes a support member, containing one or more of: a power supply; bioelectric sensors; a microprocessor and circuitry, wherein the hand piece includes a hand support member configured to be worn around a hand and is attached to the forearm piece, by a flexible membrane;
a plurality of shape memory actuators including a wrist actuator and a first set of five actuators, one at each metacarpal joint, wherein said hand piece is designed to fit between the wrist and the metacarpal joints and to support one end of the shape memory actuator for the wrist, further wherein each actuator is connected at one end to the hand piece and configured to be connected at the other end to a finger by way of a ring; and
wherein at least one ring is configured to encircle each finger, and the forearm piece reads nerve impulses through the skin of the wearer's forearm, draws the necessary electricity from batteries, and activates actuators forcing the finger(s) to move.

2. The myoelectric orthotic device of claim 1 wherein the plurality of shape memory actuators further includes a second set of actuators, the second set of actuators are connected to one end to a first set of rings and at another end to a second set of rings.

* * * * *